(12) United States Patent
Iwasa

(10) Patent No.: US 11,592,510 B2
(45) Date of Patent: Feb. 28, 2023

(54) MEDICAL APPARATUS

(71) Applicant: CANON KABUSHIKI KAISHA, Tokyo (JP)

(72) Inventor: Takeshi Iwasa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 319 days.

(21) Appl. No.: 16/524,836

(22) Filed: Jul. 29, 2019

(65) Prior Publication Data

US 2019/0361084 A1 Nov. 28, 2019

Related U.S. Application Data

(62) Division of application No. 14/407,058, filed as application No. PCT/JP2013/064961 on May 22, 2013, now Pat. No. 10,408,909.

(30) Foreign Application Priority Data

Jun. 15, 2012 (JP) .............................. JP2012-135449

(51) Int. Cl.
   *G01R 33/565* (2006.01)
   *A61B 90/11* (2016.01)
   (Continued)

(52) U.S. Cl.
   CPC ........ *G01R 33/56536* (2013.01); *A61B 5/055* (2013.01); *A61B 90/11* (2016.02);
   (Continued)

(58) Field of Classification Search
   CPC .............. G01R 33/56536; G01R 33/28; G01R 33/4808; A61B 90/11; A61B 2017/00911; A61B 2017/3409
   See application file for complete search history.

(56) References Cited

U.S. PATENT DOCUMENTS

| 6,566,991 B1* | 5/2003 | Rimkunas | G01R 33/3873 335/299 |
| 2002/0156365 A1* | 10/2002 | Tsekos | A61B 10/0233 600/411 |
| 2007/0287992 A1* | 12/2007 | Diolaiti | A61B 34/37 606/1 |

OTHER PUBLICATIONS

Chinzei K., et al., Numerical Simulations and Lab Tests for Design of MR-Compatible Robots Proceedings of the IEEE International Conference on Robotics and Automation, Orlando FL, May 2006, pp. 3819-3824.*

(Continued)

*Primary Examiner* — Bo Joseph Peng
(74) *Attorney, Agent, or Firm* — Canon U.S.A., Inc., IP Division

(57) ABSTRACT

The present invention relates to a medical apparatus which includes a motion mechanism which has at least one degree of freedom, an actuator configured to drive the motion mechanism and a control unit configured to control the actuator, and which operates in a magnetic field environment of an MRI, the medical apparatus including: a data storage unit in which data related to magnetic susceptibility of the actuator is stored; a calculating unit configured to calculate information related to an influence which the actuator exerts upon the magnetic field environment by calculation based on the magnetic susceptibility; and a communication unit configured to output the information to the MRI. An influence which an apparatus which operates in a strong magnetic field environment exerts upon an MR image can be reduced.

8 Claims, 6 Drawing Sheets

(51) Int. Cl.
*A61B 5/055* (2006.01)
*G01R 33/28* (2006.01)
A61B 17/00 (2006.01)
A61B 17/34 (2006.01)
G01R 33/48 (2006.01)

(52) U.S. Cl.
CPC .... *G01R 33/28* (2013.01); *A61B 2017/00911* (2013.01); *A61B 2017/3409* (2013.01); *G01R 33/4808* (2013.01)

(56) References Cited

OTHER PUBLICATIONS

Gruetter, Automatic, Localized in Vivo Adjustment of All First-and Second-Order Shim Coils, MRM 29:804-811, 1993.*

* cited by examiner

MEDICAL APPARATUS

CROSS-REFERENCE TO RELATED APPLICATIONS

This application is a Divisional of co-pending U.S. patent application Ser. No. 14/407,058, filed Dec. 10, 2014, which is a U.S. national stage application of International Patent Application No. PCT/JP2013/064961 filed May 22, 2013, which claims foreign priority to Japanese Patent Application No. 2012-135449, filed Jun. 15, 2012. All of the above applications are hereby incorporated by reference herein in their entirety.

TECHNICAL FIELD

The present invention relates to a medical apparatus which is operated under an environment under which a strong magnetic field is used, such as a magnetic resonance imaging apparatus.

BACKGROUND ART

A magnetic resonance imaging (MRI) apparatus provides a static magnetic field and a specific high frequency magnetic field to a measurement site of a subject, and makes an image of the inside of measurement site by applying a nuclear magnetic resonance phenomenon caused inside the measurement site.

PTL 1 discloses a visual stimulus presentation system for measuring a cerebral function using an MRI having a specific function called functional MRI. The disclosed visual stimulus presentation system includes an actuator which moves within a bore of an MRI apparatus.

NPL 1 discloses a method of puncture operation and a puncture device system using an MRI.

CITATION LIST

Patent Literature

PTL 1 Japanese Patent Laid-Open No. 2011-245202

Non Patent Literature

NPL 1 "Compact Manipulator System for Guiding Needle with Real-time Navigation Based on MR Images" Journal of Japan Society of Computer Aided Surgery Vol. 9 (2): 91-101, 2007

SUMMARY OF INVENTION

Technical Problem

In a related art technology, there has been a possibility that, when an MRI-compatible medical apparatus, such as an actuator, is disposed under a magnetic field environment, an influence upon an MR image is not sufficiently reduced.

Usually, titanium which is used as a component of a medical apparatus is generally considered as a nonmagnetic material. To the MRI, however, titanium is not necessarily a nonmagnetic material. This is because titanium has enough magnetic susceptibility to affect the MR image (about 180 parts per million (ppm)). Therefore, it is desirable that the medical apparatus is made of material having magnetic susceptibility smaller than that of titanium by at least one order (ideally, the same magnetic susceptibility as that of water, i.e., −9 ppm). However, even if the medical apparatus is made of a material which sufficiently satisfies requirements of nonmagnetism for the MRI, there are still components and parts that are not able to satisfy necessary functions by the material. For example, even if an influence upon the image may be avoided as much as possible by forming a mechanism element of the arm using resin, it is generally difficult to make a common actuator, such as a motor, using resin (except for particular cases including artificial muscle). Therefore, as long as the related art medical apparatus is disposed and is made to operate in the bore of the MRI which is the strong magnetic field environment, it is practically difficult to completely remove the influence upon the MR image in a hardware aspect.

Solution to Problem

The present invention provides a medical apparatus which reduces an influence which the medical apparatus exerts upon an MR image when the medical apparatus is operated in a strong magnetic field environment and which is compatible with the strong magnetic field environment.

The present invention provides a medical apparatus which includes a motion mechanism which has at least one degree of freedom, an actuator configured to drive the motion mechanism and a control unit configured to control the actuator, and which operates in a magnetic field environment, the medical apparatus including: a data storage unit in which data related to magnetic susceptibility of the actuator is stored; a calculating unit configured to calculate information related to an influence which the actuator exerts upon the magnetic field environment by calculation on the basis of the magnetic susceptibility; and a communication unit configured to output the information to an external device.

Advantageous Effects of Invention

According to the present invention, in a medical apparatus, such as a medical manipulator, used in combination with an external device (external medical equipment) which uses a strong magnetic field represented by an MRI, it is possible to perform precise image compensation by outputting, to the external device, compensation information on the basis of an influence of the magnetic field distortion caused by the existence of the medical apparatus in the magnetic field so that the external device can use the compensation information. Then, as the precision of the captured image is increased, the precision of diagnosis is also increased.

Further, it is possible to perform real-time image compensation on the external device side depending on the status of the dynamically changing medical apparatus by performing calculation about compensation information each time a position and a posture of the medical apparatus change, and outputting the updated calculation result to an external device via a communication unit.

Further, since image compensation can be carried out by software-based process depending on a configuration of the medical apparatus, a medical apparatus with high versatility can be provided.

Further features of the present invention will become apparent from the following description of exemplary embodiments with reference to the attached drawings.

DESCRIPTION OF EMBODIMENTS

Hereinafter, embodiments of the present invention will be described with reference to the drawings. The following embodiments do not limit the present invention related to the claims and not all the combinations of features described in the embodiments are necessary to the means for solving the present invention.

First Embodiment

Figures 1A, 1B, 1C:
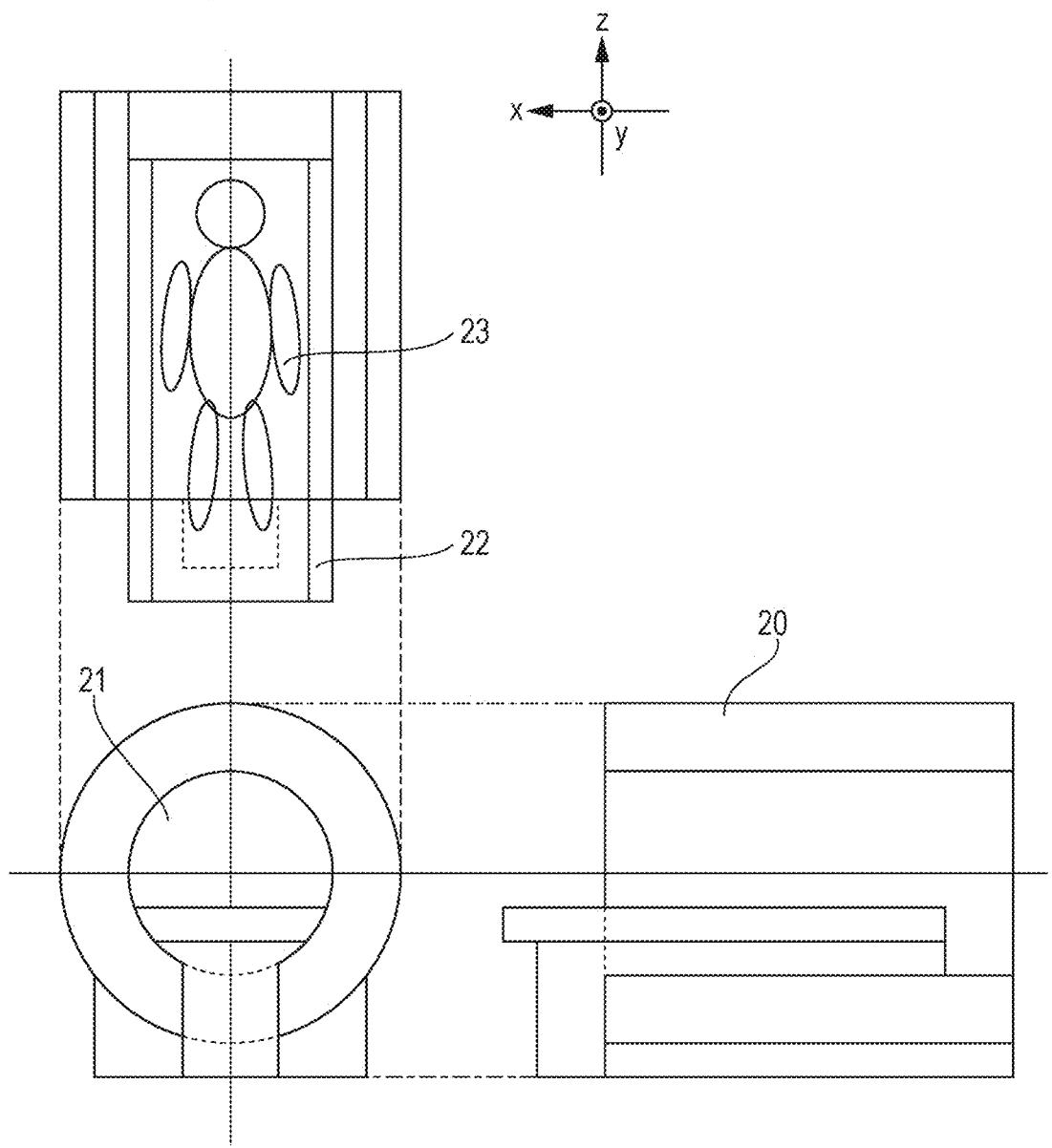
FIGS. 1A to 1C are schematic diagrams illustrating an exterior of an MRI apparatus according to the present invention.

FIGS. 1A to 1C are schematic diagrams illustrating an exterior of an MRI apparatus. FIG. 1A is a horizontal cross-sectional view, FIG. 1B is a front view and FIG. 1C is a side sectional view. A bore 21 which is an examination space of an MRI includes a circular opening. Usually, a subject (e.g., a human body) 23 is disposed on an examining table 22 in a lying position (the human body 23 is not illustrated except for the horizontal cross-sectional view of FIG. 1A). In the horizontal cross-sectional view of FIG. 1A, the direction from the leg toward the head of the human body 23 corresponds to the forward direction of a z axis in the coordinate. This direction is equivalent to the direction of the static magnetic field of an MRI 20. The MRI apparatus includes an image processing unit (not illustrated) which receives nuclear magnetic resonance signals issued by the subject 23 and generates image signals for causing an MR image inside the subject on the basis of the nuclear magnetic resonance signals to be displayed. The image processing unit compensates the image signals on the basis of information transmitted from the later-described medical apparatus which operates in a magnetic field environment inside the bore 21 (i.e., information related to an influence which the actuator of the medical apparatus exerts upon the magnetic field environment). The image signals consist of coordinates of the pixel which constitute the MR image and a pixel value. The image processing unit compensates for the coordinates of the image signals on the basis of the information related to an influence which the actuator exerts upon the magnetic field environment. Since detailed configurations and the principle of operation of the MRI apparatus are publicly known techniques, description thereof will be omitted.

Figures 2A, 2B:
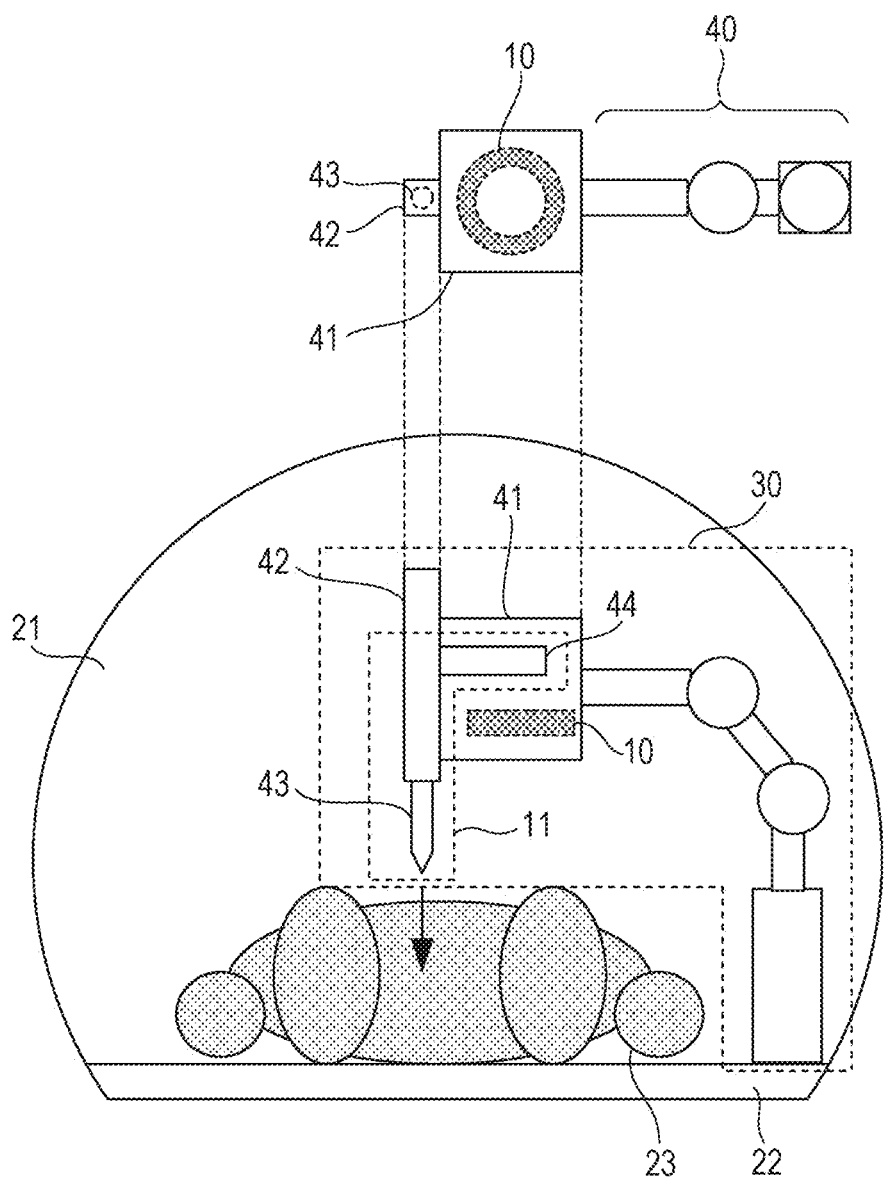
FIGS. 2A and 2B are schematic diagrams illustrating a configuration of a medical apparatus according to the present invention.

FIGS. 2A and 2B are schematic diagrams illustrating a schematic structure and exemplary installation of the medical apparatus in the bore 21. FIG. 2A is a plan view illustrating only a medical apparatus portion and FIG. 2B is a front view illustrating the inside of the bore 21 seen from the leg side of the human body 23. An inner-bore disposed portion 30 of the medical apparatus which is disposed inside the bore 21 includes a puncture needle storage unit 42 in which a puncture needle 43 is stored, a driving mechanism unit 41 in which a power transmitting unit 44 and an actuator 10 which drives the puncture needle 43 via the power transmitting unit 44 are stored, and an arm unit 40 which performs fixation and positioning of the driving mechanism unit 41 with respect to an examining table 22. As the actuator 10, an oscillatory-type actuator which uses no magnet, especially a ring-type ultrasonic motor (USM) is used. Since the principle of motion and the driving method and the like of the USM are publicly known techniques, description thereof will be omitted. By constituting components other than the actuator 10 by nonmagnetic materials, such as high intensity resin, it is possible to consider that the actuator 10 is the only element that is affecting the MR image.

Figure 3:
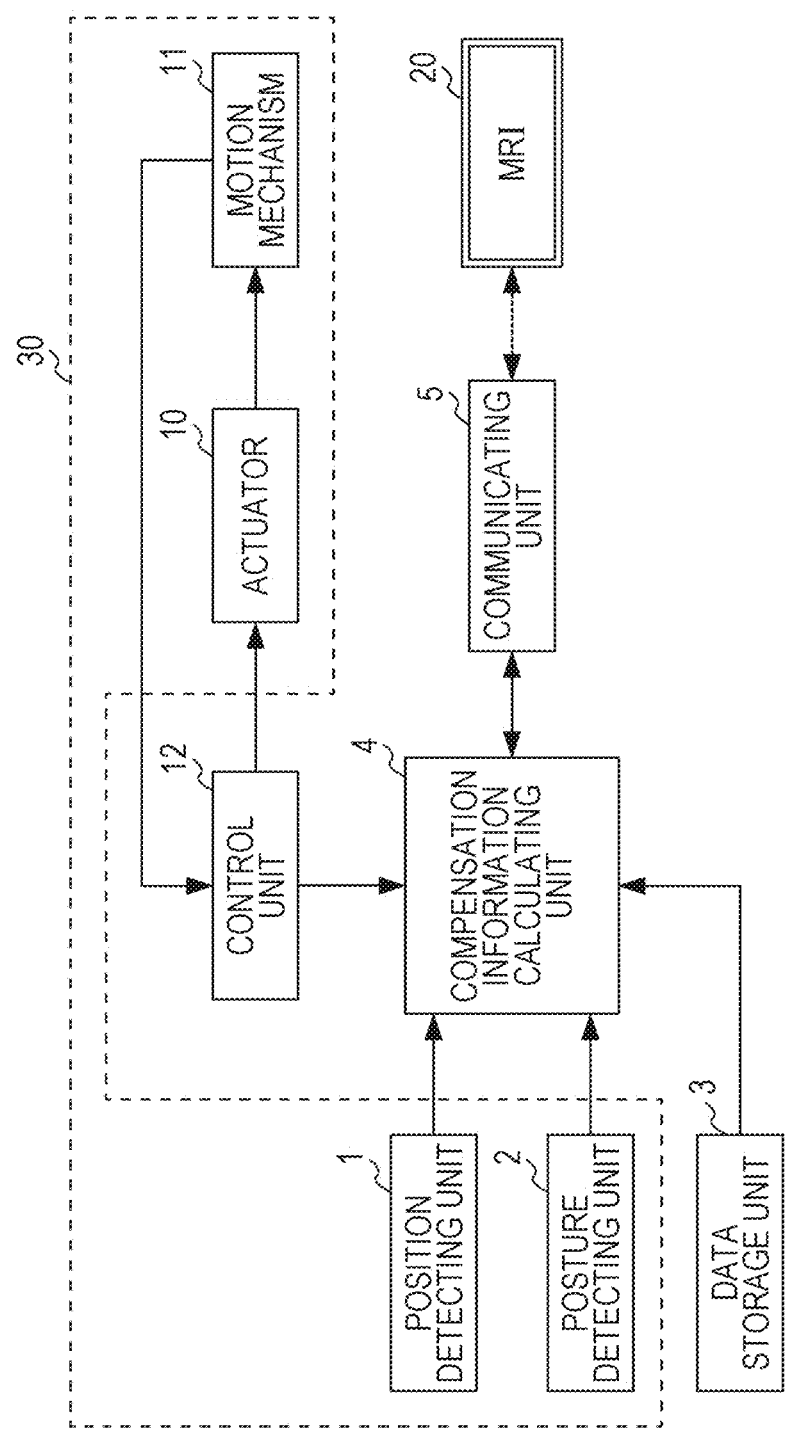
FIG. 3 is a block diagram illustrating a configuration of a medical apparatus according to the present invention.

FIG. 3 is a block diagram illustrating a configuration of the medical apparatus. It is possible to consider that the medical apparatus is a robotics system which operates under a magnetic field environment and has at least one degree of freedom. The system is divided into two blocks: a block disposed inside the bore 21 (i.e., the inner-bore disposed portion 30) is illustrated by a dotted line. Another block is disposed outside the bore 21. The MRI 20 illustrated as a double frame is an external device. A control unit 12 controls, using existing PID control, the actuator 10 for carrying out position control of an motion mechanism 11 constituted by the power transmitting unit 44 and the puncture needle 43 in accordance with an operating command output from an unillustrated command output unit. The motion mechanism 11 is a mechanism which has at least one degree of freedom including a vertical movement of the puncture needle 43 (i.e., a motion to cause the puncture needle 43 to be taken out of the puncture needle storage unit 42 and a motion to cause the puncture needle 43 to be drawn in the puncture needle storage unit 42). Position information about the puncture needle 43 detected by an unillustrated position detector is input in the control unit 12 and, on the basis of the input position information, feedback control of the motion of the puncture needle 43 is carried out. The control unit 12 outputs the position information about the puncture needle 43 to a compensation information calculating unit 4 sequentially. A position detecting unit 1 in which an optical sensor is used detects the position of the actuator 10 and outputs the position information to the compensation information calculating unit 4. A posture detecting unit 2 in which a gyro sensor is used detects a posture of the actuator 10 and outputs posture information to the compensation information calculating unit 4. A data storage unit 3 at least stores information related to magnetic susceptibility of the actuator 10 (e.g., the relative permeability, the volume, an external magnetic field and positional coordinates). A data storage unit 3 also stores in advance data necessary for calculation of compensation information, e.g., data regarding forms and data regarding magnetic susceptibility of each component of the inner-bore disposed portion 30. The communication unit 5 functions as an I/O interface between the compensation information calculating unit 4 and the MRI 20. The compensation information calculating unit 4 calculates compensation information which should be transmitted to the MRI 20 in accordance with various types of information obtained from each unit (i.e., the position detecting unit 1, the posture detecting unit 2, the data storage unit 3, the communication unit 5 and the control unit 12) and outputs the calculated compensation information to the communication unit 5. The compensation information calculating unit 4 repeats the calculation each time when at least one piece of information input from each the above-described units is updated, and each time outputs compensation information which is newly obtained calculation result to the MRI 20 via the communication unit 5.

Operation of the compensation information calculating unit 4 and transmission/reception of information between the MRI 20 will be described.

The basic content of the compensation information is, regarding at least a part of the inner-bore disposed portion 30 (hereafter, referred to as an object A), three-dimensional space distribution (magnetic field distribution information) inside the bore 21 of the magnetic field which an object A generates under an influence of the magnetic field of the MRI 20. As the object A, the actuator 10 is assumed because it is difficult to constitute the actuator 10 only by materials that do not affect an MR image, such as resin. That is, the magnetic field distribution information is information related to an influence which the actuator 10 exerts upon the magnetic field environment. Precision of MR images is increased by using such information for image generation, because the image reconstruction algorithm of the MRI 20 determines the coordinates of image information using magnetic field distribution.

Here, the image reconstruction algorithm will be described briefly. The z-coordinate of the image is a section of the human body 23 in the direction extending the head and the legs, i.e., determining the slicing position. It is determined in accordance with the magnetic field distribution in the z axial direction. And then, the x-coordinate of the image is determined by performing frequency encoding using the gradient magnetic field in the x axial direction. This uses a physical phenomenon that the resonant frequency of the nuclear magnetic resonance spin is proportional to the field strength, and so the frequency distribution in the x axial direction is proportional to a gradient magnetic field in the x axial direction. Further, the y-coordinate of the image is determined by performing phase encoding which provides skewed distribution to the phase of the nuclear magnetic resonance spin in accordance with the gradient magnetic field in the y axial direction. The phase encoding will be described briefly. First, the same gradient magnetic field as in the x axial direction makes the nuclear magnetic resonance spin have a gradient distribution of frequency for a certain period of time in the y axial direction. Then, although the resonant frequency also returns when gradient magnetic field is returned to the original, since the resonant frequency had a gradient (distribution) by the certain period of time, the phase of the nuclear magnetic resonance spin has been shifted linearly along the y-axis in accordance with the gradient magnetic field strength. The coordinates of the image are determined on the basis of the frequency and the phase encoding described above. At this time, to obtain stable images, it is required that the magnetic field has homogeneity and linearity in the order of ppm.

Next, a case in which the object A exists in the bore 21 and, thereby, distribution of the static magnetic field is not homogenous and distortion exists will be considered. Regarding the x axial direction and the z axial direction, the same distortion exists also in the distribution of the gradient magnetic field and the coordinates of the image are displaced in proportion to the distortion. Regarding the y axial direction, when a phase rotation angle produced by the phase encoding is changed in proportion to the distortion of the gradient magnetic field, the coordinates on the image are displaced. Then, by using the magnetic field distribution information about the object A as the compensation information, it is possible to compensate for picture distortion due to displacement of the pixel (i.e., the pixel and the voxel) in the image reconstruction algorithm on the MRI 20 side and to reduce an influence upon the MR image due to existence of the object A in the bore 21.

The compensation information calculating unit 4 may receive information about an imaging slice position, field of view (FOV), the static magnetic field, and the like from the MRI 20 as parameters about the external device via the communication unit 5. The compensation information calculating unit 4 may calculate compensation information using these parameters, thereby minimizing the calculation amount.

Various methods are known as methods for calculating spatial distribution of the generated magnetic field which is generated by the object A. However, it requires long time for updating the data to analyze the magnetic field with high precision using a method such as a finite element method. Therefore, it is desirable to reduce the calculation amount as much as possible using approximation in a range in which a sufficient compensation effect is obtained.

Hereinafter, the method for approximation in a case in which the actuator 10 is a ring-type USM will be described.

Figure 4A:
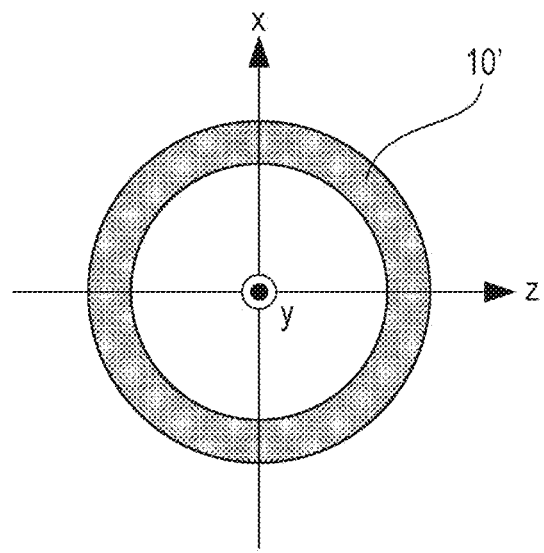
FIGS. 4A and 4B are explanatory views illustrating a concept of approximation of a ring-type USM using spheres according to the present invention.
Figure 4B:
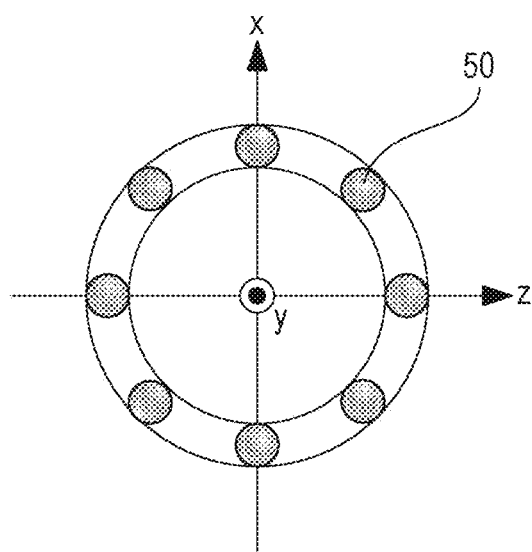

FIGS. 4A and 4B are explanatory views schematically illustrating a concept of a method for approximating the ring-type USM with a plurality of spheres. FIG. 4A illustrates a ring model 10' in which the ring-type USM is considered as a simple torus shape (i.e., a toroidal shape). FIG. 4B illustrates a sphere approximation model of the ring model 10' constituted by a plurality of spheres 50 arranged at regular intervals along in the ring shape (here, eight spheres 50 are illustrated). The center of each of the eight spheres is on a zx plane. The distance between the center and the original point is the same in the eight spheres. The centers of eight spheres are arranged at regular intervals at 45 degrees on the same circumference about the original point.

First, a case in which a single sphere exists will be considered. In this case, it is generally known that, as an influence when the external magnetic field is applied to the sphere, a model in which a magnetic moment m [Wb·m] is disposed at the center of the sphere is developed.

$$m = \frac{(\mu_r - 1)B_0 V}{1 + (\mu_r - 1)N} \quad \text{[Math. 1]}$$

In the equation, B0 represents the external static magnetic field T (tesla), μr represents the relative permeability, N represents the demagnetization factor (⅓ in a case of a sphere) and V represents the volume [m³] of the sphere. The relative permeability μr and the magnetic susceptibility χm are in the following relationships.

$$\mu r = 1 + \chi m$$

Here, in order to derive a magnetic field Bm which the magnetic moment m generates at an arbitrary point in a space, magnetic potential φ at a point situated at a distance r[m] from the point at which the magnetic moment m is placed will be considered.

$$\Phi = \frac{m \cdot r}{4\pi\mu_0 r^3} \quad \text{[Math. 2]}$$

In the equation, μ0 represents vacuum permeability and m·r represents a scalar product of a vector of m and a vector of r. The generated magnetic field Bm can be expressed by a gradient of the magnetic potential φ, and is obtained as Bm=−μ₀ grad φ. When the magnetic moment m placed at the original point is obtained on a polar coordinate with the m direction as a ground line and is converted into a Cartesian coordinates, the components of the generated magnetic field Bm are expressed by the following equations.

$$B_x = B_A \cos \Phi$$

$$B_y = B_A \sin \Phi$$

$$B_Z = \frac{\mu_r - 1}{\mu_r - 2} \cdot \frac{3\cos^2 \theta - 1}{(r/R)^3} \cdot B_0$$

[Math. 3]

The generated magnetic field Bm by the sphere 30 is expressed as a function of the distance r from the center of the sphere 30 (R: the radius of the sphere). The following equation holds.

$$B_A = \frac{\mu_r - 1}{\mu_r - 2} \cdot \frac{3\cos \theta \sin \theta}{(r/R)^3} \cdot B_0$$

[Math. 4]

Next, the above discussion will be extended to a case in which a plurality of spheres exist. It is assumed that a plurality of spheres are arranged on the zx plane as illustrated in FIG. 4B. The spheres are arranged at regular intervals with the center thereof disposed at the circumference of the radius d of the original point. When the coordinates of the center of n spheres are represented by Pi=(Pzi, Pxi), i=0, 1, . . . , n−1, the following equations hold.

$$P_{zi} = d \cos \eta = d \cos\left(\frac{2\pi}{n}i\right)$$

$$P_{xi} = d \sin \eta = d \sin\left(\frac{2\pi}{n}i\right)$$

[Math. 5]

In the above equations, η represents an angle [rad] of the vector Pi from the z axis.

On the basis of the above discussion, all the generated magnetic field by a plurality of spheres may be expressed by the linear sum of the individual generated magnetic field. That is, the above-obtained generated magnetic field Bm by the single sphere at the original point is moved in parallel so as to become a magnetic field about Pi and the sum for n spheres is obtained. As the number of spheres 50 is increased like 2, 4, 8 and 16 in a range in which the spheres do not overlap mutually, the obtained magnetic field distribution approaches a magnetic field distribution by a toroidal-shaped model.

Figure 5:
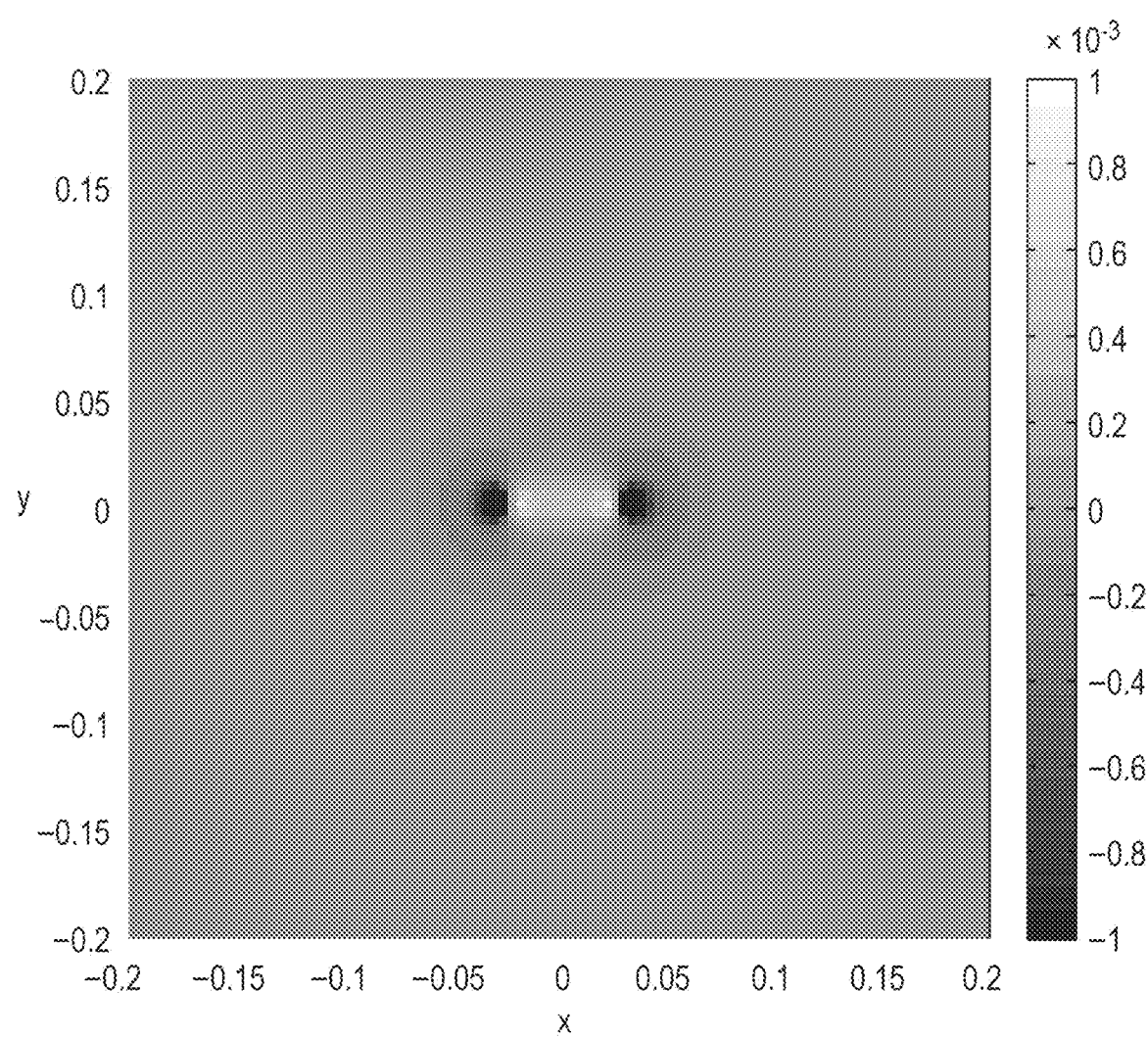
FIG. 5 is an analysis diagram illustrating a magnetic field analysis result by sphere approximation according to the present invention.

Exemplary magnetic field distribution calculated in the above-described procedure is illustrated in FIG. 5. The generated magnetic field due to 16 spheres disposed under the external magnetic field environment has been calculated for a 40-cm cube about the original point, and distribution of a z-direction component on an xy section has been plotted. The conditions of calculation are as follows: the static magnetic field B0 of the MRI 20 which is the external magnetic field is 3.0 [T]; the distance d from the original point to the center of the sphere is 3 [cm]; the radius R of the sphere is 5 [mm]; and the relative permeability μr of the sphere is 1.02. According to this approximation, in the computer environment used by the inventor, the calculation time is reduced to about one-several hundreds as compared with a case in which the generated magnetic field by the ring model 10' is calculated using the finite element method. The compensated value is fixed if there is no change in the position and the posture of the actuator 10.

As described above, it is possible to perform the compensation to reduce degradation in the MR image in the case in which an object exists in the bore by calculating an influence which the medical apparatus exerts upon the magnetic field and transmitting the calculated result to the MRI 20.

Second Embodiment

Since a basic configuration of a second embodiment other than the generation method of the compensation information and the degree of freedom of the motion mechanism is the same as that of the first embodiment, detailed description will be omitted.

Figure 6:
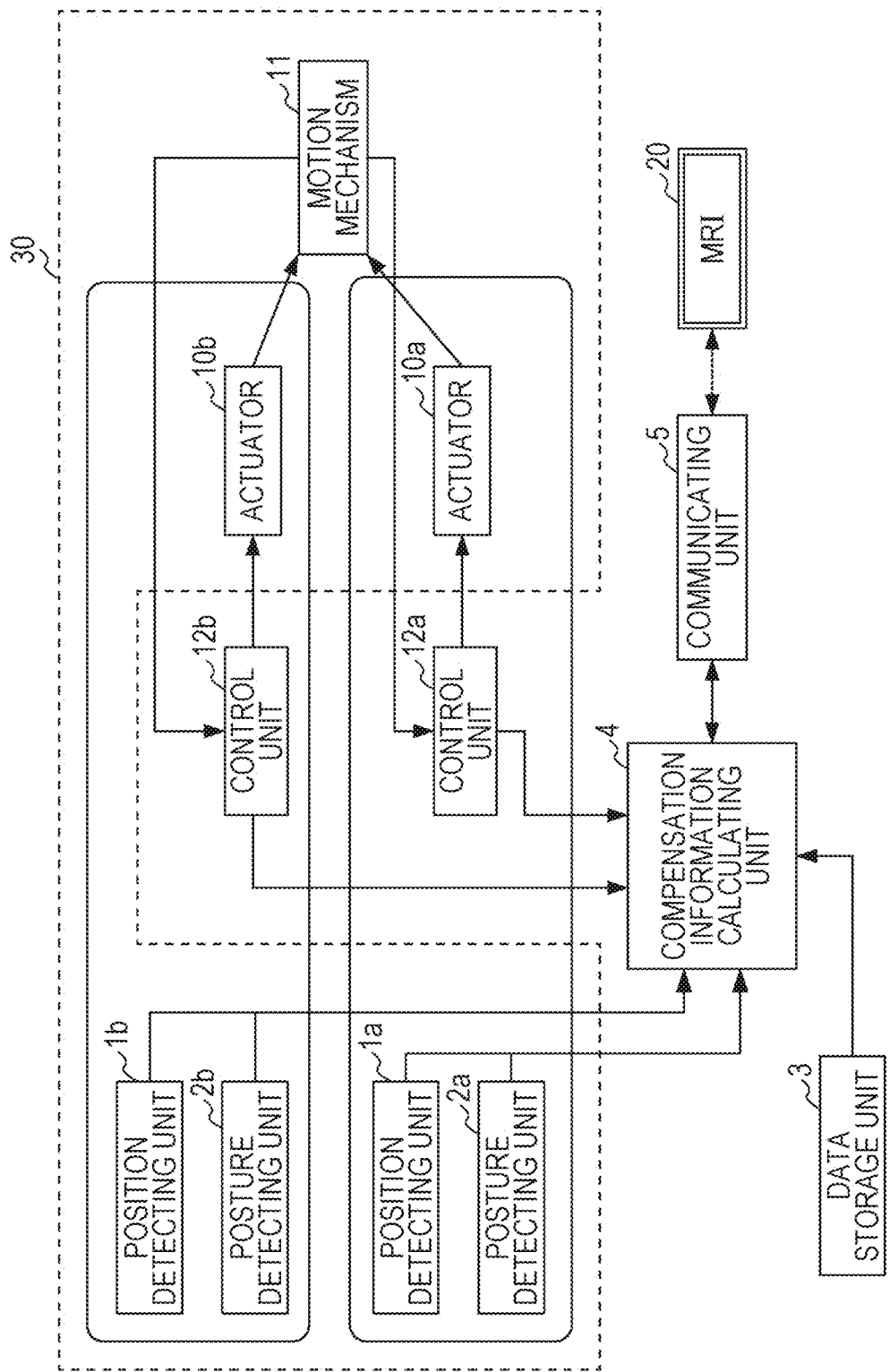
FIG. 6 is a block diagram illustrating a configuration of another medical apparatus according to the present invention.

FIG. 6 is a block diagram illustrating a configuration of a medical apparatus in the present embodiment. Unlike the first embodiment, a robotics system having two degrees of freedom is assumed in this configuration. Therefore, two sets (each having one degree of freedom of) actuators 10a and 10b, control units 12a and 12b, position detecting units 1a and 1b, and posture detecting units 2a and 2b exist, whereby a motion mechanism 11 having two degrees of freedom is moved. The motion mechanism 11 is a mechanism having at least two degrees of freedom including vertical movement of a puncture needle 43 and rotation of a puncture needle storage unit 42 in a plane including a y-axis. Since the motion mechanism 11 has two degrees of freedom, the puncture needle storage unit 42 may move like a pendulum, a human body 23 may be punctured by the puncture needle 43 from an oblique direction. For example, the medical apparatus of the present embodiment is especially advantageous in a case in which when the puncture needle 43 touches a blood vessel in front of an affected area if the human body 23 is punctured vertically.

Similarly to the first embodiment, the system of the present embodiment is also divided into two blocks and the block disposed inside the bore 21 (an inner-bore disposed portion 30) is illustrated by a dotted line. Output signals of the position detecting unit and the posture detecting unit are collectively illustrated as a single line for the convenience of illustration for each set of a and b, and are illustrated as vector signals.

In a data storage unit 3, data previously calculated by another calculation unit (personal computer) is stored as a look-up table. The data is calculated as magnetic field distribution information in accordance with the position and the posture which the motion mechanism 11 of the medical apparatus may take. The data storage unit 3 is large-capacity semiconductor memory or hard disk. Since compensation information is calculated separately, highly precise compensation information may be prepared by employing a highly precise analytic method. By previously calculating the magnetic field distribution on the assumption that the motion mechanism 11 is placed on an environment of a unit static magnetic field (for example, 1 [T]), the magnetic field distribution at this time may be applied to various static magnetic fields by multiplying the actual value of the static magnetic field of the MRI 20. The step size of the position and the posture which the motion mechanism 11 may take may be the same as that of the side of a pixel of the MR image. Alternatively, the step size may be greater than that described above and suitable interpolation may be performed for calculation at the time of actual use. Regarding the mechanism having two degrees of freedom, the magnetic field distribution data about each of the actuators 10*a* and 10*b* is stored previously in the data storage unit 3. Then, by calculating the linear sum of each magnetic field distribution data by the compensation information calculating unit 4, the magnetic field distribution data for the motion mechanism 11 may be obtained.

Each time various types of information input from each unit (the position detecting unit 1, the posture detecting unit 2, the data storage unit 3, the communication unit 5 and the control unit 12) is updated, the new compensation information is output to the MRI 20 via the communication unit 5. Since the compensation information which is origin information other than the above-described interpolation calculation is previously prepared, the time required for updating data is significantly shorter than that required in the first embodiment.

In the present embodiment, the driving mechanism has two degrees of freedom. However, the driving mechanism may have three or more degrees of freedom.

As described above, by preparing highly precise compensation information previously, real-time performance, i.e., applicability to high-speed imaging sequences of the MRI, is increased and, suitability for automation of medical practice, such as operation by an MR image feedback, is also increased.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 3 data storage unit
4 compensation information calculating unit
5 communication unit
10 actuator
11 motion mechanism
12 control unit

What is claimed is:

1. A medical apparatus comprising:
    an arm unit;
    a driving mechanism supported by the arm unit;
    a motion mechanism which has at least one degree of freedom, and is stored in the driving mechanism;
    an actuator configured to drive the motion mechanism and configured to be stored in the driving mechanism;
    a data storage unit configured to store magnetic field distribution information in accordance with position and posture of the motion mechanism, and data of a magnetic property of the actuator;
    a position detecting unit configured to detect a position of the motion mechanism; and
    a calculator that calculates position information of the motion mechanism based on an output from the position detecting unit, and calculates a three-dimensional magnetic field distribution related to an influence exerted by the actuator upon a magnetic field generated by the medical apparatus,
    wherein the calculator calculates the three-dimensional magnetic field distribution related to the influence using at least one of data of the magnetic field distribution information in accordance with position and posture of the motion mechanism and data of the magnetic property of the actuator, and
    wherein the medical apparatus is configured to generate an MR image based on image data obtained by an MRI apparatus and the three-dimensional magnetic field distribution calculated by the calculator.

2. The medical apparatus according to claim 1, wherein an influence in the MR image is decreased.

3. The medical apparatus according to claim 1, wherein the three-dimensional magnetic field distribution is distribution information of a magnetic field which the actuator generates in response to an influence of the magnetic field.

4. The medical apparatus according to claim 1, further comprising at least one posture detecting unit configured to detect a posture of the motion mechanism, wherein the calculator uses posture information output from the posture detecting unit and the position information output from the position detecting unit to calculate the three-dimensional magnetic field distribution.

5. The medical apparatus according to claim 1, wherein the calculator is configured to calculate the three-dimensional magnetic field distribution related to the influence each time when update of at least one piece of information input from a data storage is detected and output an updated result of the MR image.

6. The medical apparatus according to claim 1, wherein the actuator is an ultrasonic motor.

7. The medical apparatus according to claim 1, wherein the calculator performs a calculation which generates information on a generated magnetic field by a ring-shaped object using a combination of a plurality of spheres.

8. The medical apparatus according to claim 1, wherein the motion mechanism has two degrees of freedom.

* * * * *